United States Patent [19]

Sollevi

[11] Patent Number: 5,691,318
[45] Date of Patent: Nov. 25, 1997

[54] METHOD OF TREATING HYPEREXCITED SENSORY NERVE FUNCTION

[75] Inventor: Alf Sollevi, Bromma, Sweden

[73] Assignee: Item Development AB

[21] Appl. No.: 732,492

[22] PCT Filed: Apr. 28, 1995

[86] PCT No.: PCT/SE95/00474

§ 371 Date: Oct. 31, 1996

§ 102(e) Date: Oct. 31, 1996

[87] PCT Pub. No.: WO95/29680

PCT Pub. Date: Nov. 9, 1995

[30] Foreign Application Priority Data

May 2, 1994 [SE] Sweden .................. 9401499

[51] Int. Cl.⁶ .................. A61K 31/70
[52] U.S. Cl. .................. 514/46; 514/47
[58] Field of Search .................. 514/46, 47

[56] References Cited

U.S. PATENT DOCUMENTS

| 3,993,639 | 11/1976 | Mauvernay | 536/27 |
| 5,187,162 | 2/1993 | Marangos et al. | 514/46 |
| 5,236,908 | 8/1993 | Gruber et al. | 514/46 |

FOREIGN PATENT DOCUMENTS

| 8910744 | 11/1989 | WIPO . |
| 9323417 | 11/1993 | WIPO . |

*Primary Examiner*—Raymond Henley, III
*Attorney, Agent, or Firm*—White & Case

[57] ABSTRACT

The described invention relates to the treatment of hyperexcited sensory nerve functions, e.g., neuropathia in human subjects, comprising parenteral administration of an amount of an adenosine receptor agonist to said subjects. It is demonstrated that an adenosine receptor agonist can alleviate or normalize hyperexcited sensory nerve functions such as the perception of touch, temperature, vibration, pain, pressure and disturbances in other sensory functions.

3 Claims, 1 Drawing Sheet

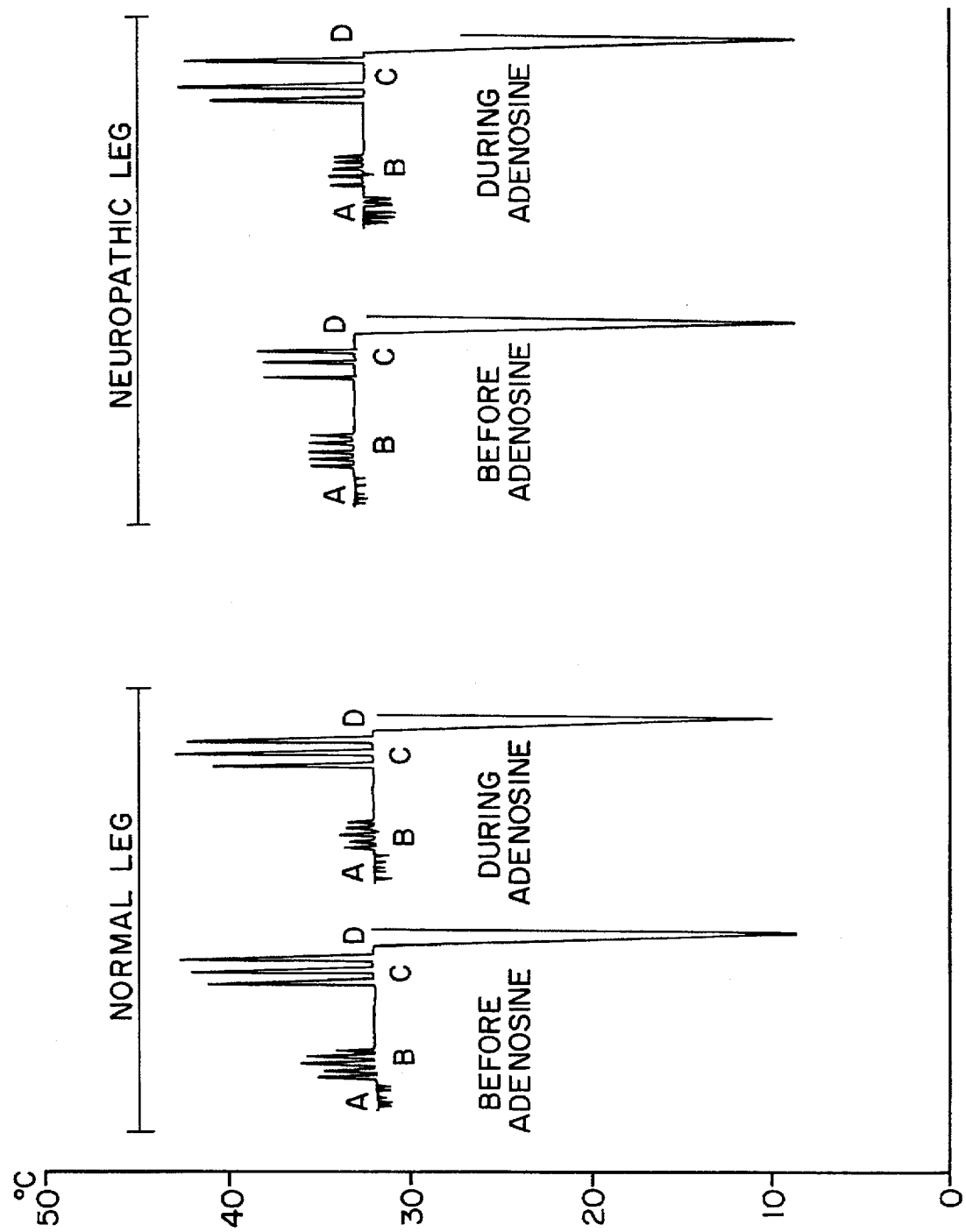

METHOD OF TREATING HYPEREXCITED SENSORY NERVE FUNCTION

This application is a 371 of PCT/SE95/00474 filed Apr. 28, 1995.

FIELD OF THE INVENTION

The present invention relates to normalization of a pathologically hyperexcited sensory nerve function in a conscious human subject. In particular, the invention relates to reduction or elimination of hyperexcited sensory symptoms.

BACKGROUND

The sensory nervous system projects signals to the central nervous system, mediating information from the periphery to the brain (CNS). These comprise signals from sensors in peripheral tissues and other organs, sensitive for qualities like touch, reduced temperature, increased temperature, vibration, painful stimuli, pressure, vision, hearing, smell, taste and balance. This sensory nervous system is an important physiological control in the subject's relation to the environment. The sensory nervous system can be damaged by various types of trauma, such as infections and mechanical lesions. This can result in disturbance in the signal transmission into the CNS, leading to reduced perception of sensory signals (hypoestesia) as well as hyperfunction (more excited signals in the CNS) due to some largely unknown changes in the nerve transmission process (neuropathic damage). The neuropathic condition with hyperexcitation is described as a "wind-up" phenomenon and often involves several of the above mentioned sensory functions. This may therefore be associated with decreased thresholds for touch and temperature (hyperesthesia), discomfort in the perception for touch and temperature (dysesthesia), discomfort or pain with touch, pressure and/or temperature stimulation (allodynia), and hypersensitivity to pain stimuli (hyperalgesia), balance disturbance, disturbance of auditory type (tinnitus) as well as ganglionic dysfunction. These types of hyperreactive sensory nerves may develop after various types of trauma, and is called chronic when persistent for more than 3–6 months. Before the present invention, there was no known specific treatment that normalizes this sensory nerve hyperreactivity. There is therefore a demand for a new principle that normalizes patients thresholds for the perception of the sensory functions touch, temperature, pain, pressure, vibration and other types of disturbances of sensory functions.

Adenosine is an endogenous nucleoside present in all cell types of the body. It is endogenously formed and released into the extracellular space under physiological and pathophysiological conditions characterized by an increased oxygen demand/supply ratio. This means that the formation of adenosine is accelerated in conditions with increased high energy phosphate degradation. The biological actions of adenosine are mediated through specific adenosine receptors located on the cell surface of various cell types, including nerves (1).

Adenosine is one of several endogenous compounds that are considered to induce pain in tissues, and application of exogenous adenosine to tissues causes pain (2,3). In the central nervous system, adenosine may act differently. The latter conclusion is based on animal data where adenosine is administered into the cerebrospinal fluid (intrathecally, i.t.) of mice after chronic implantation of a catheter close to the spinal cord. After i.t. adenosine, there is a latency in the withdrawal reflex to hot plate provocation (4). The duration of this effect is short (minutes), and it is difficult to separate this effect on latency from an adenosine-induced influence on the motor nerve functions (control of movements of the animal). Stable analogues of adenosine exert more long-lasting effects on these reflex latencies in rodents (4–6), but this is often also associated with muscle paralytic effects in the extremities. Further, endogenous adenosine has been proposed to be involved in the action of morphine, since this compound releases adenosine in the spinal cord of rats (6, review).

Adenosine is administered to human subjects for different purposes, such as vasodilation and treatment of arrhythmia. Adenosine is then given by continuous intravenous infusion or by bolus injections. Adenosine induces dose-dependent pain symptoms at intravenous infusion doses above 60 µg/kg/min or by bolus injections (3,7–10). Thus, adenosine has been demonstrated to be an algogenic compound when given i.v. in humans. The pain symptoms are located in the chest, neck, throat, head, abdomen, back, shoulder and arms (3,7–10). The incidence of dose-dependent pain at doses above 100 µg/kg/min is approximately 80% (11,12). Dose-dependent pain is produced when adenosine is infused into a peripheral arterial region in man (artery of the forearm, 13). Intradermal injection of adenosine also causes pain in healthy volunteers (2,14). Consequently, the knowledge regarding administration of adenosine to humans subjects demonstrates that it provokes dose-dependent pain symptoms. There in no information about effects of adenosine in a pathologically altered sensory nervous system.

There are experimental data that suggest that endogenous adenosine may modify sensory input at the spinal level (15). It has also been suggested that adenosine is involved in the pharmacological action of the analgesic drug morphine (6, review). There is consequently experimental information suggesting that adenosine may act physiologically in the CNS to depress noxious stimuli of the intact nervous system. After intrathecal (i.t.) adenosine administration, there is a short-lasting latency in the withdrawal reflex to hot plate provocation (4). It has also been demonstrated that adenosine infusion may reduce the surgical requirement of anesthetic drugs (inhalational anesthetics, 16,17) suggesting an interaction with anesthetic agents. It has further been proposed that adenosine has analgesic properties (inhibition or blockade of noxious stimuli, 16) without its combination with anesthetics. Thus, available data and proposals regarding the action of adenosine in the CNS relates to adenosine-induced depression of noxious stimuli as an analgesic compound. The opposite, namely a pain-inducing effect, is known from the peripheral sensory nervous system in humans. Neither of these proposed effects of adenosine is involved in the present invention, showing that adenosine infusion has the unique ability to alleviate or normalize sensory hyperexcited neuropathic conditions, without affecting any in parallel occurring hypo-excitabie neuropathic symptoms. The invention is thus not suggesting that pain mechanisms are inhibited by adenosine treatment. In contrast, the described adenosine treatment restitutes a normal perception of pain, as well as other sensory functions, in patients suffering from pathological hyperexcitation due to nerve damage.

DISCLOSURE OF THE INVENTION

The present invention relates to a method of alleviation or normalization of a pathologically hyperexcited sensory nerve function in a conscious human patient, said method comprising enteral or parenteral administration of an effective amount of an adenosine receptor agonist to said patient.

The invention also relates to the use of an adenosine receptor agonist for the manufacture of a medicament for alleviation or normalization of a pathologically hyperexcited sensory nerve function in a conscious human subject. The invention further relates to a pharmaceutical preparation for alleviation or normalization of a pathologically hyperexcited sensory nerve function in a conscious human subject, comprising an adenosine receptor agonist in a pharmaceutically acceptable carrier.

"Adenosine receptor agonists" includes compounds having an ability to effectively stimulate adenosine receptors by itself or a metabolite thereof, and is in particular adenosine and or an adenosine analogue such as R-phenyl isopropyl adenosine, N-ethyl carboxamido adenosine, as well as adenosine monophosphate, diphosphate and triphosphate. "Parenteral" is used herein in its normal sense, as excluding enteral administration such as oral or rectal administration, and in particular excluding intrathecal administration and intracerebral administration. With adenosine, parenteral administration is the preferred mode of administration.

Accordingly, the invention relates to the use of an adenosine receptor agonist as a means to reduce or eliminate neuropathic symptoms in human subjects. An adenosine receptor agonist is preferably administered by infusion. It may be administered in a central vein or preferably in a peripheral vein, by a continuous infusion during a period of at least 30 minutes. Doses given herein relate to infusion of adenosine in a peripheral vein. When adenosine is administered in a central vein, doses will be reduced to compensate for less decomposition of the compound. Adenosine may be administered in a dose of 5–150 µg/kg body weight/min. Doses above 30 µg/kg/min are particularly effective while doses below 70 µg/kg/min, by peripheral i.v. infusion are preferable since the treatment can then be conducted without causing unpleasant symptoms during the infusion period. Adenosine treatment can normalize sensory nervous function in skin areas where hyperexcitation has developed as a result of nerve damage. The effect is persistent after the treatment period, for hours to days and weeks. The treatment can be individually repeated at regular intervals or as continuous infusion e.g. with a dose pump, as a means to prevent symptoms from reoccurring. The invention is a new principle for alleviation of hypersensitivity of the sensory nerve system e.g. such as the perception of touch, temperature, vibration, pain and pressure on the skin. The invention further applies to alleviation of hyperfunction of other functions, e.g. visual function, auditory function, olfactory function, taste, balance and ganglionic transmission. The mechanism of action for the normalization of neuropathic conditions during and after i.v. adenosine administration is not known. Further, the invention can be applied to diagnosis of various types of hypersensitivity in the sensory nerve system, in order to differentiate from disturbances within the central nervous system.

Preferred embodiments of the invention will be apparent from the subsequent description and claims.

BRIEF DESCRIPTION OF THE DRAWING

The invention is further illustrated by the enclosed drawing, FIG. 1, which is a diagram recording of perception of temperature change, as well as thresholds of painful temperature stimuli, before and during i.v. adenosine infusion, determined in the damaged saphenous nerve area of the left leg in the patient of Example 2 and in the contralateral normal leg.

EXAMPLES OF TREATMENT

Example 1

A 50 year old man with a prothesis of the right distal femur due to sarcoma, was operated three months prior to the visit. The patient had a postoperative neuropathic condition as a result of surgical damage of peroneus superficialis and suralis nerves (location on the right foot), causing burning sensation upon temperature (reduced or increased) and touch stimulation. The patient had marked and reproducible allodynia and hyperalgesia before and after a 30 minute placebo infusion. The thresholds for temperature alterations (heat and cold) the thresholds for painful temperature alterations on the damaged skin area, and the contralateral normal side, were determined with a calibrated Peltiere element with computerized recordings and documentation. The thresholds for touch and painful touch were also bilaterally assessed by challenge with standardized hair filaments of increasing diameter (the von Frey technique). The patient also evaluated spontaneous pain as well as self conducted pressure at the painful skin area, by rating the experienced pain on a visual analogue scale (VAS) ranging from 0–100%. Thirty min after initiation of an i.v. adenosine infusion into a forearm, at a dose of 60 µg/kg/min, the patient had normalized perception of temperature and touch, and the pain thresholds were normalized. The self conducted pressure stimulation on the foot was experienced as essentially normal by the patient. The adenosine infusion was terminated after a 40 min infusion period. The patient had no painful sensations from the foot after termination of the treatment period. During the follow-up for 10 days, the hyperalgesia and allodynia did not return, as indication of a marked prolonged effect by the adenosine infusion treatment.

Example 2

A 24 year old woman had a postoperative neuropathic condition of the left leg after orthopaedic repair of a patella luxation, including moving bone from the left hip-bone, 14 months before the visit. The patient had hyperesthesia and hyperalgesia of the skin with aftersensation and spread in a saphenous nerve area of the left lower leg. There was also marked allodynia for heat (threshold at 38° C.). Pressure to this area was impossible due to severe pain. She also had hyperalgesia in the distal part of the cutaneous femoris lateralis nerve on the operated side. In the peroneus nerve area of the left lower leg there was a marked hypoesthesia for all tested sensations. Examinations and testings were conducted as described in Example 1. Placebo infusion for 30 min did not influence any sensory parameter, and the patient had no spontaneous resting pain. Adenosine was infused i.v. at a rate of 60 µg/kg/min for 15 min and at 50 µg/kg/min for another 25 min. The dose was reduced due to heat sensations of the head and neck.

Recordings of perception of temperature change (A—cold, B—warmth), as well as thresholds of painful stimuli (C—heat, D—cold with cut-off at 8° C.), before and during a 30 min. i.v. adenosine infusion, were determined in the damaged saphenous nerve area of the left leg and in the contralateral normal leg, and are presented in FIG. 1. The figure illustrates that adenosine treatment normalizes the heat pain threshold. Further, after 30 min of adenosine infusion, the hyperalgesia and allodynia were abolished in the saphenous area.

Thresholds for touch and pain, quantified by the von Frey technique in the damaged and normal areas described for FIG. 1 are disclosed in the table below.

TABLE

|  | Normal leg | | Neuropathic leg | |
| --- | --- | --- | --- | --- |
|  | Touch threshold (g) | Pain threshold (g) | Touch threshold (g) | Pain threshold (g) |
| Before adenosine | 0.2 | — | 0.002 | 2.7 |
| During adenosine | 0.3 | 28 | 0.3 | 28 |

As apparent from the Table, adenosine normalizes both touch and pain thresholds.

Spontaneous skin pressure by the subject was experienced as almost normal. The hyperalgesia of the cutaneous femoris lateralis nerve was also eliminated, while the hypoesthesia of the peroneus was unaffected. The patient stated that she never experienced this relief since the operation. In the follow-up, the complete normalization of nervous function lasted for six hours, declined by approximately 50% at 24 hours after treatment. At 48 hours, the patient experienced that the neuropathic problem had returned to the pretreatment level.

Example 3

A 54 year old woman had a neuropathic condition and reduced skin sensibility of the right cutaneous femoris lateralis nerve, over a period of 13 months. There was no apparent trauma to explain the nerve damage. The patient had previously been treated with a series of six regional local anaesthetic blockades to the nerve, with relief lasting for the duration of the local anaesthetic (3–4 hours). Before adenosine treatment, the patient experienced spontaneous pain (VAS 50%), hyperalgesia with aftersensations as well as spread, and allodynia for touch and heat. Examinations and testing were performed as in Example 1. Adenosine infusion (initially 50 µg/kg/min, after 20 min reduced to 40 µg due to heat sensations) lasted for 30 min. Then the hyperalgesia and allodynia for touch was essentially abolished. Spontaneous pain was reduced to 5%. The allodynia for heat was altered to a reduced and delayed sensation. The almost normalized experience from the skin area was reported to be maintained more than 24 hours, whereafter neuropathic symptoms gradually returned. At examination six days after the adenosine treatment, there were areas within the cutaneous femoris lateralis nerve innervation that still had normal sensibility, while a hyper-phenomenon was detected in other parts. The delay in heat pain perception still remained.

Example 4

Four patients (aged 38–66 years) with disabling tinnitus have received intravenous adenosine infusions and demonstrated reduced symptoms. The patients had had tinnitus since 4 to 20 years. Before adenosine administration, the patients were analyzed by a tinnitometer, i.e. an apparatus producing sound which can be varied in intensity and frequency until the patient experiences the same sound therefrom as from the tinnitus. The subjects' tinnitus was determined as to frequency (Hz) and intensity (dB). Adenosine was thereafter infused by a peripheral i.v. line at individual rates from 50 to 90 µg/kg/min for 60 minutes. Repeated determinations at 30 and 60 minutes of infusion demonstrated that the tinnitus frequency, as well as the intensity, was reduced in all patients. After termination of infusion, the patients reported reduced tinnitus symptoms during 2 up to 6 hours after treatment. Thereafter the tinnitus rapidly returned to the habitual level.

In analogy with the adenosine-induced reduction of tinnitus (Example 4) from the sensory input from the hearing organ, systemic adenosine administration would reduce vertigo induced by a pathologically high activity in the vestibularis structures of the balance organ.

BIBLIOGRAPHY

1. Burnstock G. Distribution and role of purinoreceptor subtypes. Nucleosides & Nucleotides 1991;10;917–930.

2. Bleehen T., Keele C. A. Observations on the algogenic actions of adenosine compounds on the human blister base preparation. Pain 1977;3;367–377.

3. Sylvén C., Beermann B., Jonzon B., Brandt R. Angina pectoris-like pain provoked by intravenous adenosine in healthy volunteers. Br Med J 1986;293:227–230.

4. DeLander G. E., Hopkins C. J. Involvement of A2 adenosine receptors in spinal mechanisms of antinociception. Eur J Pharmacol 1987a;139:215–223.

5. Holmgren M., Hedner J., Mellstrand T., Nordberg G., Hedner Th. Characterization of the antinociceptive effects of some adenosine analogues in the rat. Naunyn-Schmiedeberg's Arch Pharmacol 1986;334:290–293.

6. Sawynok J., Sweency M. L. The role of purines in nociception. Neuroscience 1989; 32; 557–569.

7. Sylvén C., Jonzon B., Brandt R., Beermann B., Adenosine-provoked angina pectoris-like pain—time characteristics, influence of autonomic blockade and naloxone, European Heart Journal (1987)8, 738–743.

8. Sylvén C., Jonzon B., Fredholm B. B., Kaijser L. Adenosine injection into the brachial artery produces ischaemia like pain or discomfort in the forearm. Cardiovasc Res 1988;22:674–678.

9. Crea F., El-Tamimi H., Vejar M., Kaski J. C., Davies G., Maseri A., Adenosine-induced chest pain in patients with silent and painful myocardial ischaemia: another clue to the importance of generalized defective perception of painful stimuli as a cause of silent ischaemia, European Heart Journal (1988)9 (Supplement N) 34–39.

10. Lagerqvist B., Sylvan C., Beermann B., Helmius G., Waldenström A., Intracoronary adenosine causes angina pectoris like pain—an inquiry into the nature of visceral pain, Cardiovasc Res 1990; 24: 609–13.

11. Nishimura S., Mahmarian J. J., Boyce T. M., Verani MS, Equivalence between adenosine and exercise Thallium-201 myocardial tomography: a multicenter, prospective, crossover trial. J Am Coll Cardiol 20: 265–75, 1992.

12. Abreu A., Mahmarian J. J., Nishimura S., Boyce T. M., Verani M. S., Tolerance and safety of pharmacologic coronary vasodilation with adenosine in association with thallium-201 scintigraphy in patients with suspected coronary artery disease, J Am Coll Cardiol 18: 730–735, 1991.

13. Sylvén C., Jonzon B., Fredholm B. B., Kaijser L., Adenosine injection into the brachial artery produces ischaemia like pain or discomfort in the forearm, Cardiovasc Res, 1988; 22: 674–678.

14. Pappagallo M., Gaspardone A., Tomai F., Iamele M., Crea F., Gioffré P. A., Analgesic effect of bamiphylline on pain induced by intradermal injection of adenosine, Pain 1993; 53: 199–204.

15. Salter M. W., Henry J. L., 1987, Evidence that adenosine mediates the depression of spinal dorsal horn neurons induced by peripheral vibration in the cat. Neuroscience 22, 631–650.

16. Fukunaga A., Research and Education Institute, Inc. Use of purine derivatives for anesthesia, analgesia and in vivo organ preservation. WO 91/16903, published 14 Nov. 1991.

17. Sollevi A., Adenosine infusion during isoflurane nitrous oxide anaesthesia: indications of perioperative analgesic effects. Acta Anaesthesiol Scand 1992: 36: 595–599.

I claim:

1. A method of alleviation, normalization or diagnosis of a pathologically hyperexcited sensory nerve function in a human patient, comprising administration of an effective amount of an adenosine receptor agonist to said patient, wherein said hyperexcited sensory nerve function is at least one member of the group consisting of hyperestesia and dysestesia.

2. A method of alleviation, normalization or diagnosis of a pathologically hyperexcited sensory nerve function in a human patient, comprising administration of an effective amount of an adenosine receptor agonist to said patient, wherein said hyperexcited sensory nerve function is allodynia to at least one member of the group consisting of touch, pressure, vibration, heat and cold.

3. A method of alleviation, normalization or diagnosis of a pathologically hyperexcited sensory nerve function in a human patient, comprising administration of an effective amount of an adenosine receptor agonist to said patient, wherein said hyperexcited sensory nerve function is hyperalgesia.

* * * * *